United States Patent [19]

Adam-Molina et al.

[11] Patent Number: 4,512,999
[45] Date of Patent: Apr. 23, 1985

[54] METHOD OF INHIBITING β-LACTAMASE FORMING PATHOGENS

[75] Inventors: Solange Adam-Molina, St. Louis, France; Werner Hofheinz, Bottmingen, Switzerland

[73] Assignee: Hoffmann-La Roche Inc., Nutley, N.J.

[21] Appl. No.: 312,956

[22] Filed: Oct. 20, 1981

[30] Foreign Application Priority Data

Oct. 24, 1980 [CH] Switzerland ............ 7946/80

[51] Int. Cl.³ ............... C07D 499/00; A61K 31/425
[52] U.S. Cl. ............... 514/192; 260/245.2 R; 514/195
[58] Field of Search ............ 260/245.2 T, 245.2 R; 424/270, 271

[56] References Cited

U.S. PATENT DOCUMENTS

| | | | |
|---|---|---|---|
| 4,020,077 | 4/1977 | Cook et al. | 260/245.2 R |
| 4,143,046 | 3/1979 | Sheehan | 424/270 |
| 4,207,323 | 6/1980 | Beattie et al. | 260/245.2 R |
| 4,236,001 | 11/1980 | Gleason | 344/25 |
| 4,282,149 | 8/1981 | Sheehan et al. | 424/270 |

*Primary Examiner*—Nicholas S. Rizzo
*Attorney, Agent, or Firm*—Jon S. Saxe; Bernard S. Leon; Frank P. Hoffman

[57] ABSTRACT

There are presented β-lactams of the formula

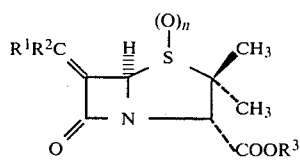

wherein $R^1$ is cyano or a group of the formula $R^4$—CO— or $R^5$—A—CO—, $R^2$ is hydrogen, lower alkyl or halogen, $R^3$ is hydrogen or a group readily cleavable by hydrolysis, n is the number 0, 1 or 2, $R^4$ is hydrogen, hydroxy, lower alkoxy, lower alkyl, aryl or a group of the formula

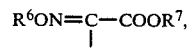

$R^5$ is halogen, lower alkoxy, lower alkylthio, lower alkylsulphinyl, lower alkylsulphonyl, aryl, aryloxy, arylthio, arylsulphinyl, arylsulphonyl or di-(loweralkoxy)phoshinyl, $R^6$ and $R^7$ are lower alkyl and A is lower alkylene, and pharmaceutically acceptable salts of carboxylic acids of formula I with bases.

The compounds exhibit pronounced β-lactamase-inhibiting properties.

12 Claims, No Drawings

METHOD OF INHIBITING β-LACTAMASE FORMING PATHOGENS

DESCRIPTION OF THE INVENTION

The present invention relates to β-lactams. In particular, it is concerned with β-lactams of the formula

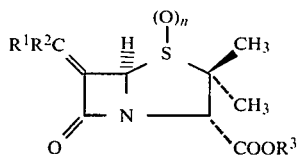

wherein $R^1$ is cyano or a group of the formula $R^4$—CO— or $R^5$—A—CO—, $R^2$ is hydrogen, lower alkyl or halogen, $R^3$ is hydrogen or a group readily cleavable by hydrolysis, n is the number 0, 1 or 2, $R^4$ is hydrogen, hydroxy, lower alkoxy, lower alkyl, aryl or a group of the formula

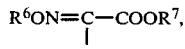

$R^5$ is halogen, lower alkoxy, lower alkylthio, lower alkylsulphinyl, lower alkylsulphonyl, aryl, aryloxy, arylthio, arylsulphinyl, arylsulphonyl or di-(lower alkoxy)phosphinyl, $R^6$ and $R^7$ are lower alkyl and A is lower alkylene,
and pharmaceutically acceptable salts of carboxylic acids of formula I with bases.

These compounds are novel and are distinguished by therapeutically valuable properties. In particular, they have pronounced β-lactamase-inhibiting properties and are therefore useful in the control of β-lactamase-forming pathogens with β-lactam antibiotics such as the penicillins and cephalosporins.

The term "group readily cleavable by hydrolysis" signifies a group cleavable under neutral, mild acidic or mild basic conditions or a group cleavable enzymatically (i.e. by an esterase). Examples of such groups, which can be of the customary kind, are alkanoyloxyalkyl groups such as pivaloyloxymethyl, acetoxymethyl, 1-pivaloyloxyethyl and 1-acetoxyethyl, alkoxycarbonyloxyalkyl groups such as methoxycarbonyloxymethyl, 1-ethoxycarbonyloxyethyl and 1-isopropoxycarbonyloxyethyl, lactonyl groups such as phthalidyl and thiophthalidyl, alkoxymethyl groups such as methoxymethyl and alkanoylaminomethyl groups such as acetamidomethyl. The term "lower alkyl", taken alone or in combinations such as in "lower alkoxy", "lower alkylthio", "lower alkylsulphinyl", "lower alkylsulphonyl" and the like signifies straight-chain or branched-chain saturated hydrocarbon groups containing at most 7, preferably at most 4, carbon atoms such as methyl, ethyl, n-propyl, isopropyl, n-butyl, s-butyl, t-butyl and the like. The term "lower alkylene" signifies straight-chain or branched-chain saturated, divalent hydrocarbon groups containing at most 4 carbon atoms such as methylene, ethylene, ethylidene, 1,2-propylene and the like. The term "lower alkoxy" embraces groups such as methoxy, ethoxy, n-propoxy, isopropoxy and the like.

The term "lower alkylthio" embraces groups such as methylthio, ethylthio, n-propylthio, i-propylthio and the like. The term "lower alkylsulphinyl" embraces groups such as methylsulphinyl, ethylsulphinyl, n-propylsulphinyl, i-propylsulphinyl and the like. The term "lower alkylsulphonyl" embraces groups such as methylsulphonyl, ethylsulphonyl, n-propylsulphonyl, i-propylsulphonyl and the like. The ethoxycarbonylmethoxyimino-methyl group is an example of a group of the formula

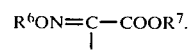

The term "aryl", taken alone or in combinations such as in "aryloxy", "arylthio", "arylsulphinyl", "arylsulphonyl" and the like signifies a phenyl group optionally substituted by halogen, nitro, hydroxy, lower alkyl or lower alkoxy, such as phenyl, p-nitrophenyl, p-bromophenyl, p-anisyl, o-hydroxyphenyl, o-tolyl, p-tolyl, 2,4-dinitrophenyl and the like. The term "halogen" signifies fluorine, chlorine, bromine and iodine.

The term "pharmaceutically acceptable salts thereof with bases" used repeatedly in this description signifies, of course, pharmaceutically acceptable salts of carboxylic acids of general formula I with bases.

The compounds of the formula I above and pharmaceutically acceptable salts thereof with bases can be present, depending on the disposition of the substituents $R^1$ or $R^2$, in the (E)- or in the (Z)-form or as mixtures of these two forms. The present invention includes not only the respective pure geometric isomers but also mixtures thereof.

Objects of the present invention are β-lactams of formula I above and pharmaceutically acceptable salts thereof with bases per se and as pharmaceutically active substances, the manufacture of these compounds and intermediates for the manufacture of these compounds, medicaments containing a compound of general formula I or a pharmaceutically acceptable salt thereof with a base and the manufacture of such medicaments, as well as the use of compounds of formula I and of pharmaceutically acceptable salts thereof with bases in the control or prevention of illnesses.

Among the compounds of formula I there are preferred those in which $R^1$ is cyano or a group of the formula $R^4$—CO— or $R^5$—A—CO—, $R^4$ is hydrogen, lower alkyl, phenyl or p-nitrophenyl, $R^5$ is chlorine, methylthio, methylsulphonyl, phenyl, phenoxy, phenylthio or phenylsulphonyl and A is methylene. $R^2$ preferably is hydrogen or halogen. $R^3$ preferably is hydrogen, acetoxymethyl or pivaloyloxymethyl. The preferred value of n is the number 0.

Quite especially preferred compounds in the scope of the present invention are:

Methylene-(2S,5R)-6-[(Z)-acetonylidene]-3,3-dimethyl-7-oxo-4-thia-1-azabicyclo[3.2.0]heptane-2-carboxylate pivalate and sodium (2S,5R)-6-[(Z)-acetonylidene]-3,3-dimethyl-7-oxo-4-thia-1-azabicyclo[3.2.0]heptane-2-carboxylate.

Further especially preferred compounds in the scope of the present invention are:

Methylene-(2S,5R)-3,3-dimethyl-6-(3-methyl-2-oxo-butylidene)-7-oxo-4-thia-1-azabicyclo[3.2.0]heptane-2-carboxylate pivalate.

methylene-(2S,5R)-3,3-dimethyl-7-oxo-6-(2-oxo-3-phenoxypropylidene)-4-thia-1-azabicyclo[3.2.0]heptane-2-carboxylate pivalate, methylene-(2S,5R)-3,3-dimethyl-7-oxo-6-(2-oxo-3-phenylpropylidene)-4-thia-1-azabicyclo[3.2.0]heptane-2-carboxylate pivalate and methylene-(2S,5R)-3,3-dimethyl-7-oxo-6-[3-methylthio-2-oxopropylidene]-4-thia-1-azabicyclo[3.2.0]-heptane-2-carboxylate pivalate.

Further preferred compounds in the scope of the present invention are:

Methylene-(2S,5R)-6-acetonylidene-3,3-dimethyl-7-oxo-4-thia-1-azabicyclo[3.2.0]heptane-2-carboxylate pivalate 4,4-dioxide, methylene-(2S,5R)-3,3-dimethyl-6-(1-chloro-2-oxopropylidene)-7-oxo-4-thia-1-azabicyclo[3.2.0]heptane-2-carboxylate pivalate, methylene-(2S,5R)-6-(3-chloroacetonylidene)-3,3-dimethyl-7-oxo-4-thia-1-azabicyclo[3.2.0]heptane-2-carboxylate pivalate, methylene-(2S,5R)-6-acetonylidene-3,3-dimethyl-7-oxo-4-thia-1-azabicyclo[3.2.0]heptane-2-carboxylate pivalate 4-oxide and (E)- and (Z)-methylene-(2S,5R)-6-(formylmethylene-3,3-dimethyl-7-oxo-4-thia-1-azabicyclo[3.2.0]heptane-2-carboxylate pivalate.

The compounds of formula I and pharmaceutically acceptable salts thereof with bases can be manufactured in accordance with the invention by (a) reacting a compound of the formula

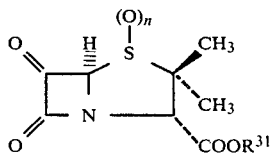

wherein $R^{31}$ is a group readily cleavable by hydrolysis and n has the above significance,
with a phosphorane of the formula

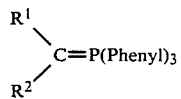

wherein $R^1$ and $R^2$ have the above significance,
or (b) oxidizing a compound of the formula

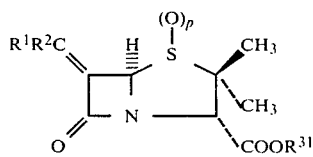

wherein p is the number 0 or 1 and $R^1$, $R^2$ and $R^{31}$ have the above significance,
at the sulphur atom(s), or (c) hydrolyzing the ester group in a compound of the formula

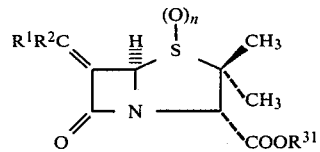

wherein $R^1$, $R^2$, $R^{31}$ and n have the above significance,
and (d) if desired, separating a mixture of the (E)- and (Z)-isomers obtained, and (e) if desired, converting a carboxylic acid of general formula I obtained with a base into a pharmaceutically acceptable salt.

In accordance with process variant (a), compounds of formula I in which $R^3$ signifies a group readily cleavable by hydrolysis and $R^1$, $R^2$ and n have the significance mentioned earlier can be manufactured by reacting a carbonyl compound of formula II in a manner known per se with a phosphorane of formula III. This reaction is conveniently carried out in an organic solvent which is inert under the reaction conditions, there primarily coming into consideration hydrocarbons such as benzene, toluene, xylene, pentane and hexane, halogented hydrocarbons such as methylene chloride, chloroform, carbon tetrachloride, 1,2-dichloroethane and chlorobenzene and ethers such as t-butyl methyl ether, tetrahydrofuran, dioxan and diethyl ether. Conveniently, the reaction is carried out in a temperature range of about 0° C. to about 50° C., preferably at room temperature.

The compound of formula II need not necessarily be used in isolated form; the reaction mixture in which it has been prepared can be processed directly in a so-called "one-pot process".

In accordance with process variant (b), compounds of formula I in which n does not signify the number 0 can be manufactured by oxidizing a compound of formula Ia at the sulphur atom, whereby a thio or sulphinyl group which may be present in the group $R^1$ (when it signifies a group of the formula $R^5$—A—CO—) can also be oxidized. This reaction can be carried out using any suitable oxidizing agent according to methods known per se. Suitable oxidizing agents for the present process aspect include peroxides such as hydrogen peroxide, t-butyl hydroperoxide and the like, and peracids such as performic acid, peracetic acid, perbenzoic acid, m-chloroperbenzoic acid, periodic acid, potassium or sodium metaperiodate and the like. Suitable solvents are, depending on the oxidizing agent used, hydrocarbons such as benzene and toluene, halogenated hydrocarbons such as dichloromethane, chloroform and 1,2-dichloroethane, lower fatty acids such as formic acid, acetic acid and the like. Depending on the reactivity of the starting material and oxidizing agent used, the reaction temperature can vary in a range of about 0° C. to the boiling point of the reaction mixture.

Depending on the oxidizing agent used and/or variations in the reaction conditions, it is readily possible to oxidize a compound of formula I in which n signifies the number 0 to a compound of general formula Ia in which n signifies the number 1. The oxidation of a sulphide of formula Ia to the corresponding sulphone can accordingly be carried out in one step or in two steps. For example, in the oxidation of a sulphide of formula Ia with about two equivalents of m-chloroperbenzoic acid in boiling dichloromethane the corresponding sulphone is obtained directly; on the other hand, if the oxidation is carried out at room temperature using about one equivalent of m-chloroperbenzoic acid, then there is obtained the corresponding sulphoxide which, if desired, can then be ozidized further to the corresponding sulphone. The choice of the suitable oxidizing agent and of the suitable reaction conditions will be readily apparent to a person skilled in the art.

In accordance with process variant (c), a carboxylic acid of formula I, i.e. a compound of formula I in which $R^3$ is hydrogen, can be manufactured by hydrolyzing the ester group in a compound of formula Ib. This hydrolysis can be carried out according to methods which are known per se and usual in such hydrolyses, whereby the choice of the suitable method and of the suitable reaction conditions will be readily apparent to a person skilled in the art.

In a preferred embodiment, the hydrolysis of a compound of formula Ib is carried out enzymatically with an esterase such as, for example; pig liver esterase in an aqueous, buffered system usual in such reactions, for example in phosphate buffer (pH 7), whereby, if desired, solubilizers such as dimethyl sulphoxide or the like can be added. The reaction temperature lies, as is usual in such cases, in a range of about 20° C. to 40° C.

In accordance with process variant (d), a mixture of the (E)- and (Z)-isomers of compounds of formula I obtained can be separated. This separation is carried out according to methods which are known per se and familiar to any person skilled in the art. Chromatography is an especially suitable method for the present process aspect.

In accordance with process variant (e), a carboxylic acid of formula I can be converted with a base into a pharmaceutically acceptable salt. Suitable bases are, for example, inorganic bases such as sodium hydroxide, sodium carbonate, sodium bicarbonte, corresponding potassium or calcium salts or the like and organic bases such as triethylamine, piperidine, diethylamine or the like. Such salts can be readily manufactured by any person skilled in the art having regard to the state of the art and the present compounds.

The compounds of formula II used as starting materials can be readily prepared, for example, from the carboxylic acid of the formula

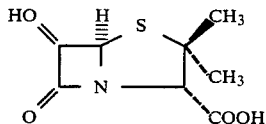   IV

In a first step, the carboxylic acid of formula IV can be converted, for example by treating a salt thereof (e.g. the sodium or potassium salt) with a suitable agent. yielding the group $R^{31}$ such as pivaloyloxymethyl iodide, acetoxymethyl iodide or the like in an inert organic solvent such as dimethylformamide, dimethylacetamide, dimethyl sulphoxide or hexamethylphosphoric acid triamide, into a compound of the formula

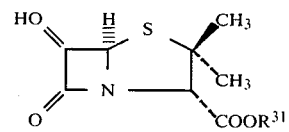   V wherein $R^{31}$ has the above significance.

by oxidizing the secondary hydroxyl group in a compound of formula V, for example with trifluoroacetic acid anhydride and dimethyl sulphoxide in an inert organic solvent, preferably in a halogenated hydrocarbon such as dichloromethane, chloroform and the like, there is obtained a compound of formula II in which n is the number 0. A thus-obtained compound can subsequently be oxidized in analogy to process variant (b), there being obtained compounds of formula II in which n is the number 1 or 2.

As mentioned earlier, the compounds of general formula I hereinbefore and pharmaceutically acceptable salts thereof with bases exhibit pronounced β-lactamase-inhibiting activities against β-lactamases from various bacteria strains. As illustrated hereinafter, these therapeutically valuable properties can be determined on isolated β-lactamases in vitro.

A. Isolation of the β-lactamases

Various β-lactamases can be isolated from penicillin-resistant or cephalosporin-resistant bacteria strains such as *Klebsiella pneumoniae* NCTC 418, *Proteus vulgaris* 1028 and *Escherichia coli* 1024. For this purpose, the corresponding strains are cultivated in Tryptic Soy Broth (Difco) and harvested by centrifugation in the late logarithmic growth phase (when required 50–100 mg/l of ampicillin are added to the medium towards the end of the log-phase in order to induce the β-lactamase). The thus-obtained bacteria mass is treated with 10 mM of phosphate buffer (pH 7.0); the cells are broken open with ultrasound (Biosonic III, Bronwill; 3–5 min. impulse) while cooling. The mixture is centrifuged (20,000 r/min.) for 20–30 minutes and there is obtained a clear crude extract which can be used as the enzyme source (β-lactamase source) and which can be frozen at −20° C. for several months without loss of activity.

B. Determination of the β-lactamase activity

The determination of the activity of the isolated β-lactamases can be carried out according to the method of O'Callaghan, C. H. et al. [Antimicr.Ag.Chemother. 1, 283–288 (1972)] with the chromogenic cephalosporin nitrocefin (87/312 of Glaxo). The required experimental batch contains per ml of water: 50 mM of phosphate buffer (pH 7.0), 0.1 mM of nitrocefin and sufficient enzyme (β-lactamase) in order to attain ΔA/min. of about 0.1. The cleavage of the substrate, which is associated with a colour change, is carried out at 37° C. and is followed quantitatively at 482 nm with a spectral photometer.

C. Determination of the β-lactamase inhibiting activity of the compounds of general formula I The above-described cleavage of the chromogenic substrate by β-lactamases (experiment B.) can be inhibited by adding compounds of general formula I (inhibitors). Since it has been shown that the inhibitors irreversibly inactivate the β-lactamase in a time-dependent reaction, the reaction (cleavage of the substrate) is started by adding the substrate, in each case after a pre-incubation period of β-lactamase with inhibitor of 15 minutes. The determination of the β-lactamase-inhibiting activity of compounds of general formula I in which $R^1$ signifies a group readily cleavable by hydrolysis is carried out in each case in the presence and absence of an esterase. As a measurement for the affinity of the respective tested inhibitor to the β-lactamase, which represents a measurement of the strength of the inhibitor, there serves that concentration which inhibits to 50% (IC 50 in μM/l) the cleavage of the substrate (nitrocefin) carried out under the above experimental conditions (experiment B.) in the absence of an inhibitor. 4 to 6 experiments with differing concentrations of inhibitor were carried out to determine the IC 50. The determination of the IC 50 was carried out graphically.

The results obtained in the above experiment (experiment C.) are given in the following Table:

Moreover, the pharmaceutical preparations can contain preserving agents, solubilizing agents, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

The carboxylic acids of formula I and their pharmaceutically acceptable salts with bases are preferably administered parenterally and for this purpose are preferably prepared as lyophilizates or dry powders. The readily hydrolyzable esters of formula I are preferably administered enterally.

As mentioned earlier, compounds of formula I and pharmaceutically acceptable salts thereof with bases can be used in accordance with the invention in the control or prevention of illnesses, especially in the control of β-lactamase-forming pathogens in combination

TABLE 1

| Products in accordance with the invention | | | | β-Lactamase inhibition: IC 50 in μM/1 | | | | | |
|---|---|---|---|---|---|---|---|---|---|
| | | | | P.v. 1028 | | K.p. NCTC 418 | | E.c. 1024 | |
| $R^1$ | $R^2$ | $R^3$ | n | −E | +E | −E | +E | −E | +E |
| CH$_3$CO— | H | Piv | 0 | 0.16 | 0.015 | 0.19 | 0.005 | 32 | 1.5 |
| CH$_3$CO— | H | H | 0 | 0.0039 | | 0.0046 | | 1.65 | |
| CH$_3$CO— | H | Piv | 1 | 0.76 | 0.16 | 28 | 1.3 | >100 | 28 |
| CH$_3$CO— | H | Piv | 2 | 1.3 | 0.51 | 1.9 | 0.18 | 18 | 1.6 |
| φ-OCH$_2$CO— | H | H | 0 | — | | 0.085 | | 0.75 | |
| NC— | H | H | 0 | 0.095 | | 14 | | 6.5 | |
| (CH$_3$)$_2$CHCO— | H | Piv | 0 | 0.25 | 0.0022 | 2.3 | 0.18 | 3.5 | 0.7 |
| φ-OCH$_2$CO— | H | Piv | 0 | 0.7 | 0.011 | 3.5 | 0.06 | 29 | — |
| φ-CH$_2$CO— | H | Piv | 0 | 0.14 | 0.011 | 0.07 | 0.0029 | >100 | 2.8 |
| CH$_3$—S—CH$_2$CO— | H | Piv | 0 | 0.6 | 0.002 | 3 | 0.065 | 55 | 3.0 |
| φ-SO$_2$—CH$_2$CO— | H | Piv | 0 | 3.5 | 0.1 | 40 | 5 | 52 | 11.5 |
| CH$_3$CO— | Cl | Piv | 0 | 0.9 | 0.62 | 4.6 | 0.22 | 4 | 0.4 |
| Cl—CH$_2$CO— | H | Piv | 0 | 0.01 | 0.032 | 7.6 | 0.46 | >100 | 8 |
| HCO— | H | Piv | 0 | 4.9 | 0.0045 | 12 | 0.7 | >100 | 16 |
| (EtO)$_2$PO—CH$_2$CO— | H | Piv | 0 | 0.055 | 0.01 | 9.4 | 1.3 | >100 | 16 |
| CH$_3$—SO$_2$—CH$_2$CO— | H | Piv | 0 | 3.1 | 0.9 | 100 | 5.2 | >100 | 20 |
| p-NO$_2$—φCO— | H | Piv | 0 | 0.53 | 0.044 | 100 | 10 | 85 | 5.5 |

−E = in the absence if an esterase
+E = in the presence of an esterase
φ = Phenyl
Piv = Pivaloyloxymethyl The compounds of formula I and pharmaceutically acceptable salts thereof with bases can be used, for example, in the form of pharmaceutical preparations. The pharmaceutical preparations can be administered orally, for example, in the form of tablets, coated tablets, dragées, hard and soft gelatine capsules, solutions, emulsions or suspensions. The administration can, however, also be carried out rectally (e.g. in the form of suppositories) or parenterally (e.g. in the form of injection solutions).

For the manufacture of tablets, coated tablets, dragées and hard gelatine capsules, the compounds of formula I and pharmaceutically acceptable salts thereof with bases can be processed with pharmaceutical inert, inorganic or organic carriers. Examples of such carriers which can be used for tablets, dragées and hard gelatine capsules are lactose, maize starch or derivatives thereof, talc, stearic acid or its salts etc. Suitable carriers for soft gelatine capsules are, for example, vegetable oils, waxes, fats, semi-solid and liquid polyols etc. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils etc. Suitable carriers for suppositories are, for example, natural or hardened oils, waxes, fats, semi-liquid or liquid polyols and the like.

with β-lactam antibiotics, i.e. antibiotics which contain a β-lactam ring, for example penicillins such as benzylpenicillin, phenoxymethylpenicillin, carbenicillin, methicillin, propicillin, ampicillin, amoxicillin and mecillinam, and cephalosporins such as cephaloridine, cephalotin, cefazolin, cephalexin, cefoxitin, cephacetrile, cephamandole, cephapirin, cephradine and cephaloglycin. Thereby, the compounds of general formula I or pharmaceutically acceptable salts thereof with bases can be administered before, simultaneously with or after the administration or intake of β-lactam antibiotics. If the compounds of formula I or pharmaceutically acceptable salts thereof with bases are administered simultaneously with a β-lactam antibiotic, then this can be carried out by administration as an ad-hoc combination or in the form of a pharmaceutical combination which contains a compound of formula I or a pharmaceutically acceptable salt thereof with a base and β-lactam antibiotic; such pharmaceutical combinations are likewise an object of the present invention.

The dosage of the compounds of formula I and the pharmaceutically acceptable salts thereof with bases can vary within wide limits and is, of course, adjusted in each particular case to the individual requirements and to the β-lactamase-producing pathogen to be controlled. In general, a daily dosage of about 0.1 to about 2.0 g should be appropriate. The ratio of β-lactamaseinhibitor (compound of formula I or pharmaceutically acceptable salt thereof with a base) to β-lactam antibiotic can also vary within wide limits and is adjusted in each particular case to the individual requirements. In general, a ratio of about 1:20 to about 1:1 should be appropriate.

As mentioned earlier, medicaments containing a compound of formula I or a pharmaceutically acceptable salt thereof with a base are also an object of the present invention as is a process for the manufacture of such medicaments which comprises bringing one or more compounds of formula I or pharmaceutically acceptable salts thereof with bases and, if desired, one or more other therapeutically valuable substances into a galenical administration form; in this connection reference is again made to the pharmaceutical combinations mentioned above which are also an object of the present invention. In particular, pharmaceutical combinations containing a compound of formula I or a pharmaceutically acceptable salt thereof with a base and a β-lactam antibiotic, for example a penicillin such as benzylpenicillin, phenoxymethylpenicillin, carbenicillin, methicillin, propicillin, ampicillin, amoxycillin and mecillinam, or a cephalosporin such as cephaloridine, cephalotin, cefazolin, cephalexin, cefoxitin, cephacetrile, cephamandole, cephapirin, cephradine and cephaloglycin, are objects of the present invention. Such combinations are suitable for the control of β-lactamase-forming pathogens.

In the following Examples, which illustrate the present invention in more detail, but are not intended to limit its extent, all temperatures are given in degrees Centigrade.

EXAMPLE 1

(a) 20 g of pivaloyloxymethyl iodide are added dropwise while stirring to an ice-cooled solution of 20 g of (2S,5R,6S)-hydroxy-7-oxo-3,3-dimethyl-4-thia-1-azabicyclo[3.2.0]heptane-2-carboxylic acid potassium salt in 50 ml of dimethylformamide. After 3 hours, the mixture is poured on to 200 g of ice and the mixture is extracted with 1000 ml of ether. The organic phase is washed neutral, dried over magnesium sulphate, filtered and evaporated. The oily residue is chromatographed on silica gel while eluting with cyclohexane/ethyl acetate (6:4). There is obtained methylene-(2S,5R,6S)-hydroxy-7-oxo-3,3-dimethyl-4-thia-1-azabicyclo[3.2.0]heptane-2-carboxylate pivalate [Rf: 0.21; cyclohexane/acetic acetate (6:4); NMR (CDCl$_3$), δ (ppm): 1.24 (9H); 1.48 (3H); 1.6 (3H); 4.5 (1H); 4.84 (1H); 5.3 (1H); 5.85 (2H)].

(b) 8.9 ml of dimethyl sulphoxide are dissolved in 150 ml of dichloromethane and the solution obtained is treated dropwise at −65° while stirring with a solution of 10.5 ml of trifluoroacetic acid anhydride in 100 ml of dichloromethane. After completion of the addition, a solution of 20.8 g of methylene-(2S,5R,6S)-hydroxy-7-oxo-3,3-dimethyl-4-thia-1-azabicyclo[3.2.0]heptane-2-carboxylate pivalate in 150 ml of dichloromethane is then added dropwise. The yellow solution obtained is subsequently stirred at −65° for 30 minutes and then treated dropwise with 20 ml of triethylamine. The reaction mixture is left to stand at room temperature, poured on to ice and extracted with dichloromethane. The combined organic phases are extracted with sodium bicarbonate solution, washed neutral, dried over magnesium sulphate, filtered and evaporated. There is obtained methylene-6,7-dioxo-3,3-dimethyl-4-thia-1-azabicyclo[3.2.0]heptane-2-carboxylate pivalate as an oily residue [Rf: 0.17; cyclohexane/ethyl acetate (6:4); NMR (CDCl$_3$), δ (ppm): 1.24 (9H); 1.53 (6H); 4.8 (1H$_3$); 5.8 (1H$_5$); 5.83 (2H)].

(c) A solution of 3.5 g of methylene-6,7-dioxo-3,3-dimethyl-4-thia-1-azabicyclo[3.2.0]heptane-2-carboxylate pivalate in 150 ml of benzene is treated at room temperature with 6.3 g of 1-triphenylphosphoranylidene-2-propanone. After 10 minutes, the reaction mixture is evaporated. The residue is chromatographed on silica gel while eluting with cyclohexane/ethyl acetate (6:4). There are obtained methylene-(2S,5R)-6-[(E)-acetonylidene]-3,3-dimethyl-7-oxo-4-thia-1-azabicyclo[3.2.0]heptane-2-carboxylate pivalate [Rf: 0.47; cyclohexane/ethyl acetate (6:4); NMR (CDCl$_3$), δ (ppm): 1.24 (9H); 1.52 (3H); 1.62 (3H); 2.62 (3H, Ac); 4.65 (1H$_3$); 5.82 (1H$_5$); 5.9 (m, 2H); 6.11 (1H)] and methylene-(2S,5R)-6-[(Z)-acetonylidene]-3,3-dimethyl-7-oxo-4-thia-1-azabicyclo[3.2.0]heptane-2-carboxylate pivalate [Rf: 0.53; cyclohexane/ethyl acetate (6:4); NMR (CDCl$_3$), δ (ppm): 1.25 (9H); 1.53 (3H); 1.61 (3H); 2.38 (3H, Ac); 4.64 (1H$_3$); 5.91 (m, 2H); 6.08 (1H$_5$): 6.63 (1H)].

EXAMPLE 2

A solution of 3.7 g of methylene-6,7-dioxo-3,3-dimethyl-4-thia-1-azabicyclo[3.2.0]heptane-2-carboxylate pivalate in 100 ml of benzene is treated at room temperature with 4.7 g of phenoxyacetylmethylenetriphenylphosphorane. After 10 minutes, the reaction mixture is evaporated. The residue is chromatographed on silica gel while eluting with cyclohexane/ethyl acetate (6:4). There is obtained methylene-(2S,5R)-3,3-dimethyl-7-oxo-6-(2-oxo-3-phenoxypropylidene)-4-thia-1-azabicyclo[3.2.0]heptane-2-carboxylate pivalate as a yellow oil [Rf: 0.44; cyclohexane/ethyl acetate (6:4); NMR (CDCl$_3$), δ (ppm): 1.21 (9H); 1.51 (3H); 1.56 (3H); 4.58 (1H); 5.66 (2H); 5.83 (2H); 6.05 (1H); 6.8–7.45 (6H)].

EXAMPLE 3

A solution of 3.2 g of methylene-6,7-dioxo-3,3-dimethyl-4-thia-1-azabicyclo[3.2.0]heptane-2-carboxylate pivalate in 150 ml of benzene is treated at room temperature with 5 g of cyanomethylenetriphenylphosphorane. After 10 minutes, the reaction mixture is evaporated. The residue is chromatographed on silica gel with cyclohexane/ethyl acetate (7:3). There are obtained methylene-(2S,5R)-6-[(Z)-cyanomethylene]-3,3-dimethyl-7-oxo-4-thia-1-azabicyclo[3.2.0]heptane-2-carboxylate pivalate as a reddish oil [Rf: 0.38; cyclohexane/ethyl acetate (6:4); NMR (CDCl$_3$) δ (ppm): 1.24 (9H); 1.53 (3H); 1.59 (3H); 4.59 (1H); 5.84 (2H); 5.89 (1H); 5.97 (1H)] and methylene-(2S,5R)-6-[(E)-cyanomethylene]-3,3-dimethyl-7-oxo-4-thia-1-azabicyclo[3.2.0]heptane-2-carboxylate pivalate as a reddish oil [Rf: 0.33; cyclohexane/ethyl acetate (6:4); NMR (CDCl$_3$), δ (ppm): 1.24 (9H); 1.51 (3H); 1.6 (3H); 4.64 (1H); 5.59 (1H); 5.84 (3H)].

EXAMPLE 4

A solution of 7.8 g of methylene-6,7-dioxo-3,3-dimethyl-4-thia-1-azabicyclo[3.2.0]heptane-2-carboxylate pivalate in 200 ml of benzene is treated at room temperature with 10 g of triphenylphosphinemethylacetylmethylene. After 10 minutes, the reaction mixture is evaporated. The residue is chromatographed on silica gel while eluting with cyclohexane/ethyl acetate (6:4). There is obtained methylene-(2S,5R)-3,3-dimethyl-6-(1-methyl-2-oxopropylidene)-7-oxo-4-thia-1-azabicyclo[3.2.0]heptane-2-carboxylate pivalate as white crystals of melting point 59°–60° [Rf: 0.30; cyclohexane/ethyl acetate (6:4)].

EXAMPLE 5

A solution of 5.4 g of methylene-6,7-dioxo-3,3-dimethyl-4-thia-1-azabicyclo[3.2.0]heptane-2-carboxylate pivalate in 100 ml of benzene is treated at room temperature with 9.6 g of phenylacetylmethylenetriphenylphosphorane. After 10 minutes, the reaction mixture is evaporated. The residue is chromatographed on silica gel while eluting with cyclohexane/ethyl acetate (6:4). There is obtained methylene-(2S,5R)-3,3-dimethyl-7-oxo-6-(2-oxo-3-phenylpropylidene)-4-thia-1-azabicyclo[3.2.0]heptane-2-carboxylate as a yellow oil [Rf: 0.4; cyclohexane/ethyl acetate (6:4); NMR (CDCl$_3$), δ (ppm): 1.23 (9H); 1.5 (3H); 1.56 (3H); 3.88 (2H); 4.58 (1H); 5.88 (2H); 6.05 (1H); 6.63 (1H); 7.37 (m, 5H)].

EXAMPLE 6

A solution of 5.4 g of methylene-6,7-dioxo-3,3-dimethyl-4-thia-1-azabicyclo[3.2.0]heptane-2-carboxylate pivalate in 100 ml of benzene is treated at room temperature with 8.8 g of dimethylacetylmethylenetriphenylphosphorane. After 10 minutes, the reaction mixture is evaporated. The residue is chromatographed on silica gel while eluting with cyclohexane/ethyl acetate (6:4). There is obtained methylene-(2S,5R)-3,3-dimethyl-6-(3-methyl-2-oxobutylidene)-7-oxo-4-thia-1-azabicyclo[3.2.0]heptane-2-carboxylate pivalate as a yellow oil [Rf: 0.35; cyclohexane/ethyl acetate (6:4); NMR (CDCl$_3$), δ (ppm): 1.12 (6H); 1.25 (9H); 1.51 (3H); 1.6 (3H); 2.77 (2H); 4.6 (1H); 5.89 (2H); 6.05 (1H); 6.72 (1H)].

EXAMPLE 7

A solution of 2.1 g of methylene-6,7-dioxo-3,3-dimethyl-4-thia-1-azabicyclo[3.2.0]heptane-2-carboxylate pivalate in 100 ml of benzene is treated at room temperature with 2.7 g of triphenylphosphine-chloroacetylmethylene. After 10 minutes, the reaction mixture is evaporated. The residue is chromatographed on silica gel while eluting with cyclohexane/ethyl acetate (6:4). There is obtained methylene-(2S,5R)-3,3-dimethyl-6-(1-chloro-2-oxo-propylidene)-7-oxo-4-thia-1-azabicyclo[3.2.0]heptane-2-carboxylate pivalate as an oil [Rf: 0.45; cyclohexane/ethyl acetate (6:4); NMR (CDCl$_3$), δ (ppm): 1.25 (9H); 1.51 (3H); 1.6 (3H); 2.53 and 2.74 (3H); 4.66 (1H); 5.9 (2H); 6.08 (1H)].

EXAMPLE 8

A solution of 3.3 g of methylene-6,7-dioxo-3,3-dimethyl-4-thia-1-azabicyclo[3.2.0]heptane-2-carboxylate pivalate in 100 ml of benzene is treated at room temperature with 6 g of phenylsulphonylacetylmethylenetriphenylphosphorane. After 10 minutes, the reaction mixture is evaporated. The residue is chromatographed on silica gel while eluting with cyclohexane/ethyl acetate (6:4). There is obtained methylene-(2S,5R)-3,3-dimethyl-7-oxo-6-[3-(phenylsulphonyl)-2-oxopropylidene]-4-thia-1-azabicyclo[3.2.0]heptane-2-carboxylate pivalate as yellow crystals of melting point 100°–102° [Rf: 0.25; cyclohexane/ethyl acetate (6:4)].

EXAMPLE 9

A solution of 4.7 g of methylene-6,7-dioxo-3,3-dimethyl-4-thia-1-azabicyclo[3.2.0]heptane-2-carboxylate pivalate in 150 ml of benzene is treated at room temperature with 9 g of p-nitrobenzoyltriphenylmethylenephosphorane. After 10 minutes, the reaction mixture is evaporated. The residue is chromatographed on silica gel while eluting with cyclohexane/ethyl acetate (6:4). There is obtained methylene-(2S,5R)-3,3-dimethyl-6-(p-nitrophenacylidene)-7-oxo-4-thia-1-azabicyclo[3.2.0]heptane-2-carboxylate pivalate as orange crystals of melting point 96°–98°.

EXAMPLE 10

A suspension of 1.7 g of methylene-(2S,5R)-6-acetonylidene-3,3-dimethyl-7-oxo-4-thia-1-azabicyclo[3.2.0]heptane-2-carboxylate pivalate in 25 ml of dimethyl sulphoxide and 500 ml of phosphate buffer (pH 7) is treated at 20° with 1.7 ml of a suspension of pig liver esterase (3 mg/ml). The mixture is stirred at 20° for 3 hours and subsequently extracted with ether. The aqueous phase is acidified (pH 3.2) with 50 percent citric acid and extracted with ether. The organic extract is washed with distilled water, dried over magnesium sulphate, filtered and evaporated. There is obtained an oily residue which is dissolved in 100 ml of ether and treated with 1.8 ml of a 2N solution of sodium 2-ethylcaptroate in ethyl acetate. The crystalline precipitate is filtered off under suction, washed with ether and dried over phosphorus pentoxide in vacuo. There is obtained sodium (2S,5R)-6-acetonylidene-3,3-dimethyl-7-oxo-4-thia-1-azabicyclo[3.2.0]heptane-2-carboxylate of melting point 150° (decomposition) [Rf: 0.31; chloroform/ethyl acetate/acetic acid (5:4:1); NMR (D$_2$O), δ (ppm): 1.58 (3H); 1.62 (3H); 2.45 (3H); 4.46 (1H); 6.12 (1H); 6.8 (1H)].

EXAMPLE 11

A solution of 3.8 g of methylene-6,7-dioxo-3,3-dimethyl-4-thia-1-azabicyclo[3.2.0]heptane-2-carboxylate pivalate in 100 ml of benzene is treated at 20° with 3.5 g of formylmethylenetriphenylphosphorane. After 10 minutes, the reaction mixture is evaporated. The residue is chromatographed on silica gel while eluting with n-hexane/ethyl acetate (8:2). There are obtained methylene-(2S,5R)-6-[(E)-formylmethylene]-3,3-dimethyl-7-oxo-4-thia-1-azabicyclo[3.2.0]heptane-2-carboxylate pivalate [Rf: 0.27; cyclohexane/ethyl acetate (8:2); NMR (CDCl$_3$), δ (ppm): 5.68 (1H$_3$); 5.9 (1H$_5$); 6.24 (1H); 10.3 (1H)] and methylene-(2S,5R)-6-[(Z)-formylmethylene]-3,3-dimethyl-7-oxo-4-thia-1-azabicyclo[3.2.0]heptane-2-carboxylate pivalate [Rf: 0.2; cyclohexane/ethyl acetate (8:2); NMR (CDCl$_3$), δ (ppm): 5.68 (1H$_3$); 6.12 (1H$_5$); 6.55 (1H); 9.86 (1H)].

EXAMPLE 12

A solution of 1.2 g of methylene-(2S,5R)-6-acetonylidene-3,3-dimethyl-7-oxo-4-thia-1-azabicyclo[3.2.0]heptane-2-carboxylate pivalate in 50 ml of dichloromethane is treated at 20° with 0.6 g of m-chloroperbenzoic acid. After 5 minutes, the mixture is washed twice with 5 percent sodium bicarbonate solution and three times with water. The organic phase is dried over magnesium sulphate, filtered and evaporated. The crystalline residue is recrystallized from ether. There is obtained methylene-(2S,5R)-6-acetonylidene-3,3-dimethyl-7-oxo-4-thia-1-azabicyclo[3.2.0]heptane-2-carboxylate pivalate 4-oxide as white crystals of melting point 148°–150°.

EXAMPLE 13

A solution of 1.5 g of methylene-6,7-dioxo-3,3-dimethyl-4-thia-1-azabicyclo[3.2.0]heptane-2-carboxylate pivalate in 50 ml of benzene is treated at room temperature with 3.1 g of triphenylphosphinebromocarboethoxymethylene. After 10 minutes, the reaction mixture is evaporated. The residue is chromatographed on silica gel while eluting with cyclohexane/ethyl acetate (6:4). There is obtained methylene-(2S,5R)-6-[bromo(ethoxycarbonyl)methylene]-3,3-dimethyl-7-oxo-4-thia-1-azabicyclo[3.2.0]heptane-2-carboxylate pivalate [mixture of the (E)- and (Z)-form] as a reddish oil [Rf: 0.5; cyclohexane/ethyl acetate (6:4); Rf: 0.1; cyclohexane/ethyl acetate (9:1); NMR (CDCl$_3$), δ (ppm): 1.25 (9H); 1.39 (3H); 1.53 (3H); 1.61 (3H); 4.18 4.6 (2H); 4.65 and 4.68 (1H); 5.7–6.1 (3H)].

EXAMPLE 14

A solution of 1.0 g of methylene-6,7-dioxo-3,3-dimethyl-4-thia-1-azabicyclo[3.2.0]heptane-2-carboxylate pivalate in 30 ml of benzene is treated at room temperature with 1.8 g of diethoxyphosphinylacetylmethylenetriphenylphosphorane. After 10 minutes, the reaction mixture is evaporated. The residue is chromatographed on silica gel while eluting with ethyl acetate. There is obtained methylene-(2S,5R)-6-[3-(diethoxyphosphinyl)-2-oxopropylidene]-3,3-dimethyl-7-oxo-4-thia-1-aza-bicyclo[3.2.0]heptane-2-carboxylate pivalate as a yellow oil [Rf: 0.35; ethyl acetate; NMR (CDCl$_3$), δ (ppm): 1.23 (9H); 1.36 (3H); 1.51 (3H); 1.59 (3H); 3.12 and 3.42 (2H, P-CH$_2$); 4.21 (4H); 4.63 (1H); 5.90 (2H): 6.08 (1H); 6.82 (1H)].

EXAMPLE 15

A solution of 6.6 g of methylene-6,7-dioxo-3,3-dimethyl-4-thia-1-azabicyclo[3.2.0]heptane-2-carboxylate pivalate in 150 ml of benzene is treated at room temperature with 9 g of triphenylchloroacetonylphosphorane. After 10 minutes, the reaction mixture is evaporated. The residue is chromatographed on silica gel while eluting with cyclohexane/ethyl acetate (7:3). There is obtained methylene-(2S,5R)-6-(3-chloroacetonylidene)-3,3-dimethyl-7-oxo-4-thia-1-azabicyclo[3.2.0]heptane-2-carboxylate pivalate as an orange oil [Rf: 0.4; cyclohexane/ethyl acetate (6:4); NMR (CDCl$_3$), δ (ppm); 1.21 (9H); 1.51 (3H); 1.57 (3H); 4.25 (2H); 4.65 (1H); 5.9 (m, 2H); 6.1 (1H); 6.93 (1H)].

EXAMPLE 16

A solution of 6.6 g of methylene-6,7-dioxo-3,3-dimethyl-4-thia-1-azabicyclo[3.2.0]heptane-2-carboxylate pivalate in 150 ml of benzene is treated at room temperature with 11 g of ethoxycarbonyl(methoxyimino)acetylmethylenetriphenylphosphorane. After 10 minutes, the reaction mixture is evaporated. The residue is chromatographed on silica gel while eluting with cyclohexane/ethyl acetate (6:4). There is obtained methylene-(2S,5R)-6-[3-ethoxycarbonyl]-2-(Z)-(methoxyimino)acetonylidene]-3,3-dimethyl-7-oxo-4-thia-1-aza-bicyclo[3.2.0]heptane-2-carboxylate pivalate as an orange oil [Rf: 0.51; cyclohexane/ethyl acetate (6:4); NMR (CDCl$_3$), δ (ppm): 1.23 (9H); 1.37 (m, 3H); 1.53 (3H); 1.62 (3H); 4.21 (3H, —OCH$_3$); 4.42 (m, 2H); 4.65 (1H$_3$); 5.9 (m, 2H); 6.11 (1H); 6.66 (1H)].

EXAMPLE 17

A solution of 1.2 g of methylene-(2S,5R)-6-acetonylidene-3,3-dimethyl-7-oxo-4-thia-1-azabicyclo[3.2.0]heptane-2-carboxylate pivalate in 50 ml of dichloromethane is treated at 20° with 1.2 g of m-chloroperbenzoic acid. The mixture is heated to boiling under reflux for 4 hours. The reaction mixture is cooled, extracted with 5 percent sodium bicarbonate solution and washed neutral with water. The organic phase is dried over magnesium sulphate, filtered and evaporated. There is obtained methylene-(2S,5R)-6-acetonylidene-3,3-dimethyl-7-oxo-4-thia-1-azabicyclo[3.2.0]heptane-2-carboxylate pivalate 4,4-dioxide as yellow crystals of melting point 120°–122° [Rf: 0.20; cyclohexane/ethyl acetate (6:4)].

EXAMPLE 18

A solution of 2.3 g of methylene-6,7-dioxo-3,3-dimethyl-4-thia-1-azabicyclo[3.2.0]heptane-2-carboxylate pivalate in 75 ml of benzene is treated at room temperature with 4 g of methylsulphonylacetylmethylenetriphenylphosphorane. After 10 minutes, the reaction mixture is evaporated. The residue is chromatographed on silica gel while eluting with cyclohexane/ethyl acetate (1:1). There is obtained methylene-(2S,5R)-3,3-dimethyl-7-oxo-6-[3-methylsulphonyl-2-oxopropylidene]-4-thia-1-azabicyclo[3.2.0]heptane-2-carboxylate pivalate as an orange oil [Rf: 0.23; cyclohexane/ethyl acetate (1:1); NMR (CDCl$_3$), δ (ppm): 1.22 (9H); 1.5 (3H); 1.56 (3H); 3.03 (3H, CH$_3$—SO$_2$); 4.24 (2H, —CH$_2$—SO$_2$); 4.59 (1H); 6.02 (1H); 6.79 (1H)].

EXAMPLE 19

A solution of 5.2 g of methylene-6,7-dioxo-3,3-dimethyl-4-thia-1-azabicyclo[3.2.0]heptane-2-carboxylate pivalate in 100 ml of benzene is treated at room temperature with 8 g of thiomethylacetylmethylenetriphenylphosphorane. After 10 minutes, the reaction mixture is evaporated. The residue is chromatographed on silica gel while eluting with cyclohexane/ethyl acetate (6:4). There is obtained methylene-(2S,5R)-3,3-dimethyl-7-oxo-6-[3-methylthio-2-oxopropylidene]-4-thia-1-azabicyclo[3.2.0]heptane-2-carboxylate pivalate as an orange oil [Rf: 0.53; cyclohexane/ethyl acetate (6:4); NMR (CDCl$_3$), δ (ppm): 1.21 (9H); 1.49 (3H); 1.56 (3H); 2.02 (3H, CH$_3$—S—); 2.25 (2H, S—CH$_2$); 4.53 (1H); 5.78 (2H); 5.99 (1H); 6.75 (1H)].

EXAMPLE 20

34 ml of dimethyl sulphoxide are dissolved in 500 ml of dichloromethane, the solution obtained is treated dropwise at −65° and while stirring firstly with a solution of 40 ml of trifluoroacetic acid anhydride in 300 ml of dichloromethane and then with a solution of 79 g of methylene-(2S,5R,6S)-hydroxy-7-oxo-3,3-dimethyl-4-thia-1-azabicyclo[3.2.0]heptane-2-carboxylate pivalate in 300 ml of dichloromethane. The yellow solution obtained is subsequently stirred at −65° for 30 minutes and then treated dropwise with 76 ml of triethylamine. The reaction mixture is left to stand at room temperature and the brown solution obtained is treated with 98 g of acetylmethylenetriphenylphosphorane. After 10 minutes, the reaction mixture is evaporated. The residue is chromatographed on silica gel while eluting with cyclohexane/ethyl acetate (7:3). There is obtained methylene-(2S,5R)-5-acetonylidene-3,3-dimethyl-7- oxo-4-thia-1-azabicyclo[3.2.0]heptane-2-carboxylate pivalate.

EXAMPLE 21

A suspension of 2.2 g of methylene-(2S,5R)-3,3-dimethyl-6-(3-methyl-2-oxobutylidene)-7-oxo-4-thia-1-azabicyclo[3.2.0]heptane-2-carboxylate pivalate in 300 ml of dimethyl sulphoxide and 500 ml of phosphate buffer (pH 7.1) is treated at 20° with 2 ml of a suspension of pig liver esterase (3 mg/ml). The reaction mixture is stirred at 20° for 2 hours and subsequently extracted with ether. The aqueous phase is acidified (pH 3.2) with 50% citric acid and extracted with ether. The organic extract is washed with distilled water, dried over magnesium sulphate, filtered and evaporated. There is obtained an oily residue which is dissolved in 200 ml of ether and treated with 2.4 ml of a 2M solution of sodium 2-ethylcaproate. The crystalline precipitate is filtered off under suction, washed with ether and dried over phosphorus pentoxide in vacuo. There is obtained sodium (2S,5R)-3,3-dimethyl-6-(3-methyl-2-oxobutylidene)-7-oxo-4-thia-1-azabicyclo[3.2.0]heptane-2-carboxylate of melting point 145° (decomposition). [$R_f$ 0.41; chloroform/ethyl acetate/acetic acid (5:4:1); NMR (D$_2$O) δ (ppm); 1.17 (6H); 1.53 (3H); 1.61 (3H); 2.95 (1H); 4.4 (1H); 6.05 (1H); 6.9 (1H)].

EXAMPLE 22

1.1 ml of dimethyl sulphoxide are dissolved in 20 ml of dichloromethane, the solution obtained is treated dropwise at −65° while stirring firstly with a solution of 1.3 ml of trifluoroacetic acid anhydride in 10 ml of dichloromethane and then with a solution of 2.4 g of methylene-(2S,5R,6S)-hydroxy-7-oxo-3,3-dimethyl-4-thia-1-azabicyclo[3.2.0]heptane-2-carboxylate acetate in 20 ml of dichloromethane. The yellow solution obtained is subsequently stirred at −65° for 30 minutes and then treated dropwise with 2.45 ml of triethylamine. The reaction mixture is left to stand at room temperature and the brown solution obtained is treated with 3.2 g of acetylmethylenetriphenylphosphorane. After 5 minutes, the reaction mixture is evaporated. The residue is chromatographed on silica gel while eluting with cyclohexane/ethyl acetate (6:4). There is obtained methylene-(2S,5R)-6-acetonylidene-3,3-dimethyl-7-oxo-4-thia-1-azabicyclo[3.2.0]heptane-2-carboxylate acetate [$R_f$ 0.21; cyclohexane/ethyl acetate (6:4); NMR (CDCl$_3$), δ (ppm); 1.51 (3H); 1.59 (3H); 2.13 (3H); 2.36 (3H); 4.6 (1H); 5.83 (2H); 6.03 (1H); 6.57 (1H)].

EXAMPLE 23

A solution of 7.9 g of methylene-6,7-dioxo-3,3-dimethyl-4-thia-1-azabicyclo[3.2.0]heptane-2-carboxylate pivalate in 150 ml of benzene is treated at 20° with 10.6 g of thiophenylacetylmethylenetriphenylphosphorane. After 5 minutes, the reaction mixture is evaporated. The residue is chromatographed on silica gel while eluting with cyclohexane/ethyl acetate (7:3). There is obtained methylene-(2S,5R)-3,3-dimethyl-7-oxo-6-[3-phenylthio-2-oxopropylidene]-4-thia-1-azabicyclo[3.2.0]heptane-2-carboxylate pivalate as an orange oil [$R_f$ 0.34; cyclohexane/ethyl acetate (7:3): NMR (CDCl$_3$) δ (ppm): 1.21 (9H); 1.48 (3H); 1.56 (3H); 3.73 (2H); 4.57 (1H); 5.8 (2H); 5.95 (1H); 6.88 (1H); 7.35 (5H)].

What is claimed:

1. A method of inhibiting beta-lactamase forming pathogens in an individual in need of such treatment which comprises treating said individual with an effective amount of a compound of the formula

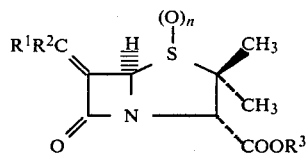

wherein $R^1$ is cyano or a group of the formula $R^4$—CO— or $R^5$—A—CO, $R^3$ is hydrogen, lower alkyl or halogen, $R^3$ is hydrogen or a group selected from alkanoyloxyalkyl, alkoxycarbonyloxyalkyl, lactonyl, alkoxymethyl and alkanoylaminomethyl, n is the number 0, 1 or 2, $R^4$ is hydrogen, hydroxy, lower alkoxy, lower alkyl, phenyl or phenyl substituted by halogen, nitro, hydroxy, lower alkyl or lower alkoxy or a group of the formula

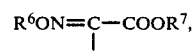

$R^5$ is halogen, lower alkoxy, lower alkylthio, lower alkylsulphinyl, lower alkylsulphonyl, di-(lower alkoxy)-phosphinyl, phenyl or phenyl substituted by halogen, nitro, hydroxy, lower alkyl or lower alkoxy, phenyloxy, phenylthio, phenylsulphinyl, phenylsulphonyl or phenyloxy, phenylthio, phenylsulphinyl and phenylsulphonyl substituted by halogen, nitro, hydroxy, lower alkyl or lower alkoxy, $R^6$ and $R^7$ are lower alkyl and A is lower alkylene,
and pharmaceutically acceptable salts of carboxylic acids of formula I with bases.

2. A method of inhibiting beta-lactamase forming pathogens in an individual in need of such treatment which comprises treating said individual with an effective amount of a compound of the formula: Methylene-(2S,5R)-6-[(Z)-acetonylidene]-3,3-dimethyl-7-oxo-4-thia-1-azabicyclo[3.2.0]heptane-2-carboxylate pivalate.

3. A method of inhibiting beta-lactamase forming pathogens in an individual in need of such treatment which comprises treating said individual with an effective amount of a compound of the formula: Sodium (2S,5R)-6-[(Z)-acetonylidene]-3,3-dimethyl-7-oxo-4-thia-1-azabicyclo[3.2.0]heptane-2-carboxylate.

4. A method of inhibiting beta-lactamase forming pathogens in an individual in need of such treatment which comprises treating said individual with an effective amount of a compound of the formula: Methylene-(2S,5R)-3,3-dimethyl-6-(3-methyl-2-oxobutylidene)-7-oxo-4-thia-1-azabicyclo[3.2.0]heptane-2-carboxylate pivalate.

5. A method of inhibiting beta-lactamase forming pathogens in an individual in need of such treatment which comprises treating said individual with an effective amount of a compound of the formula: Methylene-(2S,5R)-3,3-dimethyl-7-oxo-6(2-oxo-3-phenoxypropylidene)-4-thia-1-azabicyclo[3.2.0]heptane-2-carboxylate pivalate.

6. A method of inhibiting beta-lactamase forming pathogens in an individual in need of such treatment which comprises treating said individual with an effective amount of a compound of the formula: Methylene-(2S,5R)-3,3-dimethyl-7-oxo-6-(2-oxo-3-phenylpropylidene)-4-thia-1-azabicyclo[3.2.0]heptane-2-carboxylate pivalate.

7. A method of inhibiting beta-lactamase forming pathogens in an individual in need of such treatment which comprises treating said individual with an effective amount of a compound of the formula: Methylene-(2S,5R)-3,3-dimethyl-7-oxo-6-[3-methylthio-2-oxopropylidene]-4-thia-1-azabicyclo[3.2.0]heptane-2-carboxylate pivalate.

8. A method of inhibiting beta-lactamase forming pathogens in an individual in need of such treatment which comprises treating said individual with an effective amount of a compound selected from the group consisting of methylene-(2S,5R)-6-acetonylidene-3,3-dimethyl-7-oxo-4-thia-1-azabicyclo[3.2.0]heptane-2-carboxylate pivalate 4,4-dioxide; methylene-(2S,5R)-3,3-dimethyl-6-(1-chloro-2-oxopropylidene)-7-oxo-4-thia-1-azabicyclo[3.2.0]heptane-2-carboxylate pivalate; methylene-(2S,5R)-6-(3-chloroacetonylidene)-3,3-dimethyl-7-oxo-4-thia-1-azabicyclo[3,2,0]heptane-2-carboxylate pivalate; methylene-(2S,5R)-6-acetonylidene-3,3-dimethyl-7-oxo-4-thia-1-azabicyclo[3.2.0]heptane-2-carboxylate pivalate 4-oxide and (E)- and (Z)-methylene-(2S,5R)-6-(formylmethylene)-3,3-dimethyl-7-oxo-4-thia-1-azabicyclo[3.2.0]heptane-2-carboxylate pivalate.

9. The method of claim 1, wherein $R^1$ is cyano or a group of the formula $R^4$—CO— or $R^5$—A—CO—, $R^4$ is hydrogen, lower alkyl, phenyl or p-nitrophenyl, $R^5$ is chlorine, methylthio, methylsulphonyl, phenyl, phenoxy, phenylthio or phenylsulphonyl and A is methylene.

10. The method of claim 9, wherein $R^2$ is hydrogen or halogen.

11. The method of claim 10, wherein $R^3$ is hydrogen, acetoxymethyl or pivaloyloxymethyl.

12. The method of claim 11 wherein n is the number 0.

* * * * *